United States Patent [19]

Wildnauer et al.

[11] 4,294,852
[45] Oct. 13, 1981

[54] SKIN TREATING COMPOSITIONS

[75] Inventors: Richard H. Wildnauer, East Brunswick; William T. Humphries, Pennington, both of N.J.

[73] Assignee: Johnson & Johnson, New Brunswick, N.J.

[21] Appl. No.: 607,171

[22] Filed: Aug. 21, 1975

Related U.S. Application Data

[63] Continuation-in-part of Ser. No. 411,939, Nov. 1, 1973, abandoned.

[51] Int. Cl.³ ............................................. A61K 31/19
[52] U.S. Cl. ................................... 424/317; 424/150; 424/164; 424/168; 424/177; 424/181; 424/234; 424/240; 424/245; 424/250; 424/273 R; 424/274; 424/275; 424/280; 424/285; 424/318
[58] Field of Search ................... 424/317, 343, 61, 70, 424/318, 150, 164, 177, 181, 234, 285, 168, 240 245, 274, 280, 275, 273 R

[56] References Cited

U.S. PATENT DOCUMENTS

| | | | |
|---|---|---|---|
| 1,700,035 | 1/1929 | Ellis | 424/343 |
| 2,118,566 | 5/1938 | Miles | 424/317 X |
| 2,217,905 | 10/1940 | Hoffman et al. | 424/317 |
| 2,809,913 | 10/1957 | Hoff | 424/343 X |
| 3,218,234 | 11/1965 | Wilmsmann et al. | 424/70 |
| 3,257,280 | 6/1966 | Richter | 424/61 |
| 3,335,053 | 8/1967 | Weitzel | 424/317 |
| 3,349,000 | 10/1967 | Joos | 424/61 |
| 3,510,554 | 5/1970 | Balsiger | 424/61 |
| 3,666,863 | 5/1972 | Swanbeck | 424/317 |
| 3,755,560 | 8/1973 | Dickert et al. | 424/78 |
| 3,879,537 | 4/1975 | Van Scott et al. | 424/317 X |

OTHER PUBLICATIONS

Van Scott et al., II, *Arch Dermatology* 110:586–590, (1974).
Wahlberg et al., *Acta Dermatovener* (Stockholm) 53:207–210, (1973).
Middleton, *J. Soc. Cosmet. Chem.* 25, 519–534, (1974).
Scheuplein et al., I, *J. Soc. Cosmet. Chem.* 21, 853–873, (1970).
Scheuplein et al., II, *Physiological Reviews*, vol. 51, No. 4, pp. 702–747 (1971).

*Primary Examiner*—Robert Gerstl
*Assistant Examiner*—Vera C. Clarke
*Attorney, Agent, or Firm*—Irving Newman

[57] ABSTRACT

The invention relates to a composition for treatment and control of excessively thickened, inflexible and scaly stratum corneum which often fissures into the dermis resulting in foci of bleeding and inflammation which are symptomatic of numerous altered skin conditions. More specifically, this invention relates to a composition comprising an aqueous phase comprising water in which are dissolved one or more aliphatic alcohols selected from the group consisting of n-propanol and the monohydric aliphatic alcohols having from 4 to about 8 carbon atoms, preferably n-butanol, n-pentanol and n-hexanol, in combination with one or more organic acids selected from the group consisting of the saturated aliphatic, mono, di-and tri-carboxylic acids having from 2 to about 10 carbon atoms, including those acids which are substituted at either or both of the alpha and beta carbons with a hydroxyl or keto functionality. The composition is also an excellent vehicle for topically active drugs or other skin treating agents. Optionally, the composition of the invention may include a minor amount of a lipid phase.

13 Claims, No Drawings

SKIN TREATING COMPOSITIONS

CROSS REFERENCE TO RELATED APPLICATION

This application is a continuation-in-part of copending application Ser. No. 411,939, filed Nov. 1, 1973, now abandoned.

BACKGROUND OF THE INVENTION

Stratum corneum, the outer layer of skin, is a multicellular membrane of flattened, metabolically active cells. In living animals, the membrane is dynamic, in that surface cells are lost through desquamation but replaced at an equivalent rate from the underlying epidermal cells to maintain a thickness of a constant number of cells in the stratum corneum. Alterations in the rate of desquamation can result in a thickened, less flexible corneum.

To function normally as a diffusion and mechanical barrier, the stratum corneum must be sufficiently strong and flexible to reversibly sustain large deformations without fracturing. This elasticity is a function of both the configuration of the keratinous fibrous components of the cells and the presence of plasticizers, principally water. When not properly plasticized, the membrane becomes less flexible, and surface cells fail to desquamate normally, producing scale formation and surface roughness. Dry skin conditions ranging in severity from mild chapping to ichthyosis and psoriasis have been shown to be associated with macromolecular and morphological defects involving insufficient plasticization which may be responsible for the lack of flexibility and associated scaling and roughness. Accordingly, effective treatment to relieve or prevent the symptoms of these dry skin conditions requires physically altering or restoring the plasticized conditions of the macromolecular keratinous material and promoting desquamation of the irreversibly altered surface cells.

A description of a related therapy for scaly skin appeared in a recent publication by E. Van Scott and R. Yu in Arch. Dermatology 110:586–590 (1974) and more recently in Van Scott et al. U.S. Pat. No. 3,879,537 issued Apr. 22, 1975. The therapy is for control of keratinization with alpha-hydroxy acids and related compounds. The composition and method of the present invention differ from Van Scott et al. in employing the aliphatic alcohols in combination with the acids. Thus, Van Scott et al. did not find or teach what we have discovered—that the combination of their acids with n-propanol or a $C_4$-$C_8$ aliphatic alcohol is significantly more effective in clearing the scales and cracking of dry skin than an equivalent concentration of acid alone. The only alcohols which appear to be mentioned in the Van Scott patent are ethanol and isopropanol. The use of alcohols in accordance with the present invention permits the use of significantly lower concentrations of these acids than described in the Van Scott patent. Moreover, while all acids disclosed by Van Scott et al. are suitable for use in the compositions of the present invention, we have found that numerous other organic acids have beneficial value in our compositions.

Swanbeck U.S. Pat. No. 3,666,863 relates to a skin treating composition comprising an aqueous solution of urea (2 to 30%) and lactic acid (0.5 to 8%). Swanbeck suggests that although urea alone is useful in treating dry skin, its combination with the alpha hydroxy acid, lactic acid, is more effective. However, we have found in tests on heavily scaled elbows and knees that, at comparable concentrations, the combination of lactic acid and urea with n-butanol was significantly more effective than the combination of urea and lactic acid alone. Moreover, we have found that when we combine an alcohol with the acid and urea in accordance with our invention, we require substantially less acid and urea than the amounts preferred by Swanbeck.

The combination of an aliphatic alcohol and an organic acid would not be expected to be an effective treatment for dry skin conditions since aliphatic alcohols and organic acids are not highly hygroscopic; alcohols are considered to have a drying effect on the skin surface, and the combination does not form a water impermeable film to prevent water loss from the tissue. Moreover, structurally closely related alcohols to those employed in the compositions and method of the present invention do not afford these beneficial effects. Thus, ethanol and isopropanol, commonly used in cosmetic formulations, have been found to be ineffective when employed as the alcohol in the compositions and method of the present invention. Similarly, inorganic acids such as HCl and $H_2SO_4$ are not nearly as effective as the presently claimed acids, nor are many organic acids such as formic or acetic acid, when employed as the acid in the composition of the present invention, illustrating that these beneficial effects are not a result merely of the acidic pH of the composition.

The composition and method of the present invention are not directed at primary underlying causes of faulty keratinization in the conditions discussed above, but rather at relieving the discomfort of associated scales and ensuing cracking and bleeding. The essential property of the present skin treating composition is that it promotes the loss of the altered surface corneum cells while it increases corneum flexibility so that further cracking is reduced, allowing any existing lesions to heat without further mechanical injury.

SUMMARY OF THE INVENTION

In accordance with the present invention, symptomatic scaling and cracking associated with numerous conditions of the skin such as chapping, atopic dermatitis, ichthyosis, psoriasis and dandruff are alleviated or prevented by the periodic topical application to the skin area to be protected or treated of an effective amount of a composition comprising a major amount of an aqueous phase comprising water having dissolved therein at least one alcohol selected from the group consisting of n-propanol and the lower saturated aliphatic alcohols having from 4 to about 8 carbon atoms, e.g. n-butanol, n-pentanol and n-hexanol, in combination with one or more organic acids selected from the group consisting of the saturated aliphatic mono-, di- and tri-carboxylic acids and the derivatives of said carboxylic acids which are substituted at one or both of the alpha and beta carbons with a hydroxyl or keto functionality.

The compositions should have a pH of from about 2 to 6.5, preferably from about 2.5 to about 5.

The skin treating compositions according to the invention may optionally contain a lipid phase as the dispersed phase in the continuous aqueous phase. As the lipid, saponifiable and also non-saponifiable lipids may be used as well as wool fat, paraffin oil, petrolatum or other lipid products commonly used in cosmetic and pharmaceutical creams and lotions. The amount of the lipid phase should not exceed 15% by weight of the skin treating composition.

The novel composition can also be useful as a vehicle for topical application of other skin treating agents, including such pharmaceutical compounds as steroids, anti-microbials, etc. The descaling action of the composition allows for more efficient sorption of the topical skin treating agent by the stratum corneum barrier cells, while the rapid hydrating and softening action immediately following topical application of the composition promotes the deposition of the skin treating agent into the upper layers of the corneum and its subsequent penetration through the epidermis. Thus, the composition and method of this invention provide rapid hydration of the stratum corneum (which hydration is known to enhance penetration of topical agents) without the need for occlusion by water impermeable films. Moreover, the more effective deposition and penetration of skin treating agents from the composition of this invention allows the use of lower concentrations of skin treating agents, often avoiding irritation and other undesirable side effects of higher doses.

Thus, the present invention provides a skin treating composition comprising at least a major amount of an aqueous phase comprising water having dissolved therein at least one alcohol selected from the group consisting of n-propanol and the lower saturated aliphatic alcohols having from 4 to about 8 carbon atoms in combination with one or more organic acids selected from the group consisting of the saturated aliphatic, mono, di- and tri-carboxylic acids and the derivatives of said carboxylic acids which are substituted at one or both of the alpha and beta carbons with a hydroxyl or keto functionality.

The invention further provides improved pharmaceutically active compositions comprising the composition defined above in combination with a topically active pharmaceutical compound.

In another aspect, the invention provides a method of alleviating or preventing the symptomatic scaling and cracking associated with various conditions of the skin, this method comprising the periodic topical application to the skin area to be protected or treated of an effective amount of the skin treating composition defined above.

In yet another aspect, the invention provides a method for enhancing the activity of a known topically active pharmaceutical compound comprising incorporating said compound in the skin treating composition defined above.

DESCRIPTION OF THE PREFERRED EMBODIMENTS

The compositions of this invention comprise an aqueous solution of an alcohol selected from the group consisting of n-propanol, and the aliphatic monohydric alcohols having from 4 to about 8 carbon atoms, and an organic acid having 2 to 10 carbon atoms selected from the group consisting of the saturated aliphatic monocarboxylic acids, dicarboxylic acids and tricarboxylic acids, including those of said acids having a hydroxyl or keto functionality at either or both of the alpha and beta carbons, said substituted acids being preferred.

Preferred aliphatic carboxylic acids are the linear, primary aliphatic acids containing from 3 to about 8 carbon atoms. Of this group, propionic, valeric and caproic acid have been found to provide particularly effective compositions.

The dicarboxylic acids employed in the compositions of the present invention are preferably those having from 2 to about 8 carbon atoms, more preferably those containing substituents selected from hydroxyl and keto groups at either or both of the alpha and beta carbons. Particularly preferred linear saturated dicarboxylic acids are oxalic, malonic, succinic, adipic and pimelic. Glutaric acid is another useful member of this group. Examples of suitable hydroxyl substituted dicarboxylic acids include saccharic, mucic, malic and tartaric acids, with malic acid being particularly preferred. A useful hydroxyl substituted tricarboxylic acid is citric acid.

The alpha-hydroxy mono-carboxylic acids are particularly effective as the organic acid in the compositions of the present invention. Preferably, these acids have from 2 to about 8 carbon atoms, more preferably from about 3 to about 5. Lactic acid (alpha-hydroxy propionic acid) and alpha-hydroxy butyric acid are particularly preferred examples of this class of acids. Glyceric acid is an example of a useful alpha, beta-dihydroxy carboxylic acid. Beta-hydroxy butyric acid examplifies a useful beta-substituted acid.

The preferred keto acids are glyoxylic acid, pyruvic acid and acetoacetic acid.

The concentrations of the acid in the compositions may range from 0.1 to about 5%, more preferably from about 0.2 to about 2%, by weight of the acid based on the weight of the entire composition.

The alcohols which may be employed in the composition of the present invention are n-propanol and the aliphatic monohydric alcohols having from 4 to about 8 carbon atoms. The straight chain alcohols having 4–6 carbon atoms are preferred. Particularly preferred is n-butanol.

Branched, cylic and aromatic derivatives of these alcohols, while generally less effective than the parent compounds, also may be used in accordance with the present invention. These include tert.-butyl alcohol, sec.-butyl alcohol, isopentyl alcohol, cyclohexanol and benzyl alcohol.

The concentration of the alcohol in the compositions depends on the alcohol selected and will generally vary from 0.1% to about 35% by weight, based on the weight of the composition. The concentration of n-propanol may vary from about 10 to about 35%, and is preferably about 30%, by weight; n-butanol may be employed in concentrations varying from about 0.1 to 15% by weight, preferably from about 3 to 8% by weight; n-pentanol may be employed in the range of about 0.1 to 5%, preferably about 2.3%; and the range for n-hexanol will be from about 0.1% to about 2.5%, with a concentration of 0.6% being preferred.

The aqueous alcohol-organic acid compositions of this invention may be used "as is" (in a single, aqueous phase) or may optionally also contain a minor amount of a lipid phase as the disperse phase, with the aqueous phase being the continuous phase. In formulating a suitable composition, a wide variety of materials and formulations generally known to the art may be used in combination with the aqueous alcohol-organic acid composition, provided that the aqueous phase predominates as the continuous phase. Desirably, the lipid phase does not exceed about 15% by weight of the total composition. Preferably, the lipid phase comprises no more than about 5% by weight of the composition.

The composition of the invention may contain, in addition to the alcohol, acid and water, such preservatives, oils and adjuvants as ethoxylated lanolin derivatives (for example, the Solulan Series available commercially from American Cholesterol Co., e.g., Solulan 98) mineral oil, isopropyl palmitate, stearyl alcohol, cetyl alcohol, sodium stearoyl lactylate, e.g., Emplex (Atlas Chemical Co.), hydroxyethyl cellulose, a carboxy vinyl polymer, e.g., Carbopol 940, sorbic acid, propylene glycol, sugar alcohol esters, as well as perfumes, coloring agents and the like.

In another aspect of the present invention, the composition of the present invention may be employed as a vehicle for a topically active pharmaceutical compound, which enhances the topical activity of said compound, i.e., permits the use of lower concentrations to achieve the same activity or affords increased activity at the same concentration as compared to prior art vehicles.

Examples of active compounds for which the compositions of the present invention can be employed as vehicles include retinoic acid; urea; ascorbic acid; propylene glycol; selenium sulfide; salicylic acid; pyrrolidone 5-carboxylic acid; the anti-inflammatory corticosteroids such as hydrocortisone, betamethosone benzoate, desflurotriamcinolone, triamcinolone acetonide, dexamethasone, dexamethasone acetate, flumethasone pivalate, flumethasone valerate and deprodone propionate; the topically active non-steroidal anti-inflammatory agents including such inhibitors of prostaglandin synthetase as bufexemac (p-n-butoxyphenylacethydroxamic acid), suprofen (p-2 thenoyl hydratropic acid); the antibiotics such as tetracycline, oxytetracycline, chlorotetracycline, neomycin, erythromycin, bacitracin, steptomycin, and chloromycetin; the anti-fungal agents such as griseofulvin, mycostatin, miconazole and miconazole nitrate; the antimitotics such as metholtrexate; bisdiguanides such as chlorohexidine; quaternary ammonium compounds such as domiphen bromide, benzalkonium chloride, cetyl pyridinium chloride, dequalinium chloride, cetyl trimethyl ammonium bromide as well as benzethonium chloride and methylbenzethonium chloride as described in U.S. Pat. Nos. 2,170,111 and 2,115,250; the carbanilides and salicylanilides such as 3,4,4'-trichlorocarbanilide, and 3,4,5-tribromosalicylanilide; the hydroxydiphenyls such as dichlorophene, tetrachlorophene, hexachlorophene, and 2,4,4'-trichloro-2'-hydroxydiphenylether; and organometallic and halogen antiseptics such as zinc pyrithione, iodine, and the iodophores derived from non-ionic surface active agents as described, for example, in U.S. Pat. Nos. 2,710,277 and 2,977,315 and from polyvinylpyrrolidone as described, for example, in U.S. Pat. Nos. 2,706,701, 2,826,532 and 2,900,305.

The manner of formulating the composition will be apparent to those skilled in the art and will, of course, depend upon the specific ingredients employed and the nature of the vehicle. As is apparent, the alcohol, water and acid may be readily combined with gentle stirring.

In use, the composition of the invention is applied topically to the skin area to be treated or protected, at regular intervals, as needed, generally from about 7 to about 21 times per week. The duration of the treatment will depend upon the nature and severity of the condition to be treated as well as the frequency of application of the composition. In general, however, improvement is noticeable within the first week or two, with a nearly normal appearing and feeling skin surface present within four weeks. Continuous, less frequent application of the composition will maintain this improved state.

The following examples are presented to further illustrate the invention without thereby limiting the scope thereof.

EXAMPLE 1

| Ingredients | % (By Weight) |
|---|---|
| n-butanol | 6.0 |
| Urea | 5.0 |
| Lactic acid | 0.1 |
| Water | 88.9 |
| | 100.0 |

EXAMPLE 2

| Ingredients | % (By Weight) |
|---|---|
| n-butanol | 6.0 |
| Malic acid | 2.0 |
| Water | 92.0 |
| | 100.0 |

EXAMPLE 3

| Ingredients | % (By Weight) |
|---|---|
| Oil Phase | |
| Ethoxylated lanolin derivative (Solulan 98) | 1.00 |
| Mineral oil | 1.60 |
| Isopropyl palmitate | 0.90 |
| Stearyl alcohol | 0.5 |
| Cetyl alcohol | 0.5 |
| | 4.50 |
| Water Phase | |
| Water (steam distilled) | 84.75 |
| Urea | 5.0 |
| n-butanol | 5.0 |
| Hydroxyethyl cellulose (Natrosol 25OH) | 0.3 |
| Carboxy vinyl polymer (Carbopol 942) | 0.2 |
| Lactic acid | 0.5 |
| Sorbic acid (preservative) | 0.2 |
| The pH of this composition is about 4.0 | 95.5 |

EXAMPLE 4

| Ingredients | % (By Weight) |
|---|---|
| Oil Phase | |
| Isopropyl palmitate | 2.00 |
| Stearyl alcohol | 0.05 |
| Cetyl alcohol | 1.00 |
| Sodium stearoyl lactylate | 1.00 |
| | 4.05 |
| Water Phase | |
| Sorbic acid | 0.20 |
| Carboxy vinyl polymer | 0.50 |
| n-butanol | 5.00 |
| Urea | 5.00 |
| Propylene glycol | 3.00 |
| Lactic acid | 0.20 |
| Water q.s. | to 100.00 |

As will be apparent to those skilled in the art, many variations and modifications may be made without departing from the spirit and scope of the invention.

What is claimed is:

1. A skin treating composition comprising (a) a major amount of an aqueous phase comprising water having dissolved therein from about 0.1 to about 35% by weight of said composition of an alcohol selected from the group consisting of n-propanol and the monohydric aliphatic alcohols having from 4 to 6 carbon atoms, and an effective amount, sufficient to adjust the pH of said composition to a pH within the range of about 2 to about 6.5, of an organic acid having from 2 to about 10 carbon atoms selected from the group consisting of the aliphatic mono-, di- and tri-carboxylic acids and the derivatives of said acids which are substituted at one or both of the alpha and beta carbons with a hydroxyl or keto group; and (b) no more than about 15% by weight of the total composition of a lipid phase.

2. The composition of claim 1, wherein said lipid phase comprises a saponifiable or non-saponifiable lipid selected from the group consisting of wool fat, paraffin oil, petrolatum and other pharmaceutically acceptable lipid materials.

3. The composition of claim 2, where the lipid phase does not exceed 10% by weight of the total composition.

4. The composition of claim 2, where the lipid phase does not exceed 5% by weight of the total composition.

5. The composition of claim 1, further comprising an effective amount of a topically active pharmaceutical compound.

6. The composition of claim 5, wherein said pharmaceutical compound is selected from the group consisting of retinoic acid, the anti-inflammatory corticosteroids, the topically active non-steroidal anti-inflammatory agents, antifungal agents and antimitotics, and the topically effective quaternary ammonium compounds, bis-diguanidines, carbanilides, salicylanilides, hydroxydiphenyls and organometallic antiseptics.

7. The composition of claim 5, wherein said pharmaceutical compound is selected from the group consisting of retinoic acid, urea, ascorbic acid, propylene glycol, selenium sulfide, salicylic acid, pyrrolidone 5 carboxylic acid, hydrocortisone, betamethasone benzoate, desfluorotriamcinolone, triamcinolone acetonide, dexamethasone, dexamethasone acetate, flumethasone pivalate, flumethasone valerate, deprodone propionate, bufexemac, suprofen, tetracycline, oxytetracycline, chlorotetracycline, neomycin, erythromycin, bacitracin, streptomycin, chloromycetin, griseofulvin, mycostatin, miconazole, miconazole nitrate, metholtrexate, chlorhexidine, domiphen bromide, benzalkonium chloride, cetyl pyridinium chloride, dequalinium chloride, cetyl trimethyl ammonium bromide, benzethonium chloride, methylbenzethonium chloride, 3,4,4'-trichlorocarbanilide, 3,4,5-tribromosalicylanilide, dichlorophene, tetrachlorophene, hexachlorophene, 2,4,4'-trichloro-2'-hydroxydiphenylether, zinc pyrithione, iodine and the iodophores derived from non-ionic surface active agents and from polyvinylpyrrolidone.

8. The composition of claim 5, wherein said pharmaceutical compound is retinoic acid.

9. The composition of claim 5, wherein said pharmaceutical compound is selected from the group consisting of the antibiotics and the halogen antiseptics.

10. A method for alleviating or preventing symptomatic scaling and cracking of the skin, comprising applying to the skin an effective amount of the composition of claim 1.

11. The method of claim 10, wherein said composition is applied at regular intervals from about 7 to about 21 times weekly.

12. The method of claim 11, wherein said composition contains from about 0.1% to about 5% based on the weight of the composition of an alcohol selected from the group consisting of n-butanol, n-pentanol and n-hexanol.

13. The method of claim 12, wherein said composition contains from about 0.1% to about 5% based on the weight of the composition of an acid selected from the group consisting of propionic, valeric, caproic, oxalic, malonic, succinic, adipic, pimelic, malic, lactic, alpha-hydroxy-butyric, pyruvic, betahydroxy-butyric, acetoacetic, glyceric, glycolic, citric and tartaric acids.

* * * * *